(12) United States Patent
Watts et al.

(10) Patent No.: US 6,562,820 B2
(45) Date of Patent: May 13, 2003

(54) METHOD FOR TREATMENT AND PREVENTION OF MASTITIS

(75) Inventors: Jeffrey L. Watts, Portage, MI (US); Margaret S. Sanchez, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/888,634

(22) Filed: Jun. 23, 2001

(65) Prior Publication Data

US 2002/0111349 A1 Aug. 15, 2002

Related U.S. Application Data

(60) Provisional application No. 60/215,900, filed on Jul. 5, 2000.

(51) Int. Cl.[7] ............... A61K 31/535; A61K 38/16; A61K 31/42
(52) U.S. Cl. ............... 514/235.5; 514/236.8; 514/376; 514/8
(58) Field of Search ............ 514/235.5, 236.8, 514/376, 8

(56) References Cited

U.S. PATENT DOCUMENTS

| | | | |
|---|---|---|---|
| 5,688,792 A | 11/1997 | Barbachyn et al. | 514/235.5 |
| 6,040,306 A | 3/2000 | Batts et al. | 514/236.8 |

FOREIGN PATENT DOCUMENTS

| | | | |
|---|---|---|---|
| WO | WO 95/07271 | 3/1995 | C07D/263/20 |
| WO | WO 98/54161 | 5/1998 | 6/263.2 |
| WO | WO 99/37630 | 7/1999 | |
| WO | WO 99/62504 | 12/1999 | |
| WO | WO 00/03710 | 1/2000 | |

OTHER PUBLICATIONS

Smith KL, Olivery SP, *Exp. Med. Biol,* 137:535–554 (1981).

Lohuis, J.A.C.M., Hesen SM, and Beers H, pp. 110–111 in Proc. 3$^{rd}$ (1986).

Naidu AS, Arnold RR, *Diagn. Microbiol. Infect. Dis,* 20:69–75 (1994).

Sanchez MS, Watts JL, *J Dairy Sci.,* 82: 494–499 (1999).

Linezolid, Oxazolidinone Antibacterial Drugs of the Future, 1996, 21(11): 1116–1123, XP 000654643.

*Primary Examiner*—Kevin E. Weddington
(74) *Attorney, Agent, or Firm*—Austin W. Zhang

(57) ABSTRACT

The invention is directed to a method of treatment or prevention of mastitis in mammals with known oxazolidinone anti-bacterial agents, either alone or in combination with exogenous lactoferrins.

31 Claims, No Drawings

METHOD FOR TREATMENT AND PREVENTION OF MASTITIS

CROSS-REFERENCE TO RELATED APPLICATIONS

This application claims the benefit of the U.S. provisional application Serial No. 60/215,900 filed Jul. 5, 2000 under 35 U.S.C. §119(e)(i).

BACKGROUND OF THE INVENTION

1. Field of the Invention

The present invention relates to the treatment and prevention of mastitis with known oxazolidinones, alone or in combination with exogenous lactoferrins.

2. Description of the Related Art

Mastitis, which has been known and treated for many years, is an inflammatory disease of the mammary gland of a mammal caused by infection of a multitude of bacteria. Bovine mastitis is one of the most difficult cattle diseases to deal with and is of considerable economic significance to the dairy industry. Bovine mastitis may be caused by Gram-negative bacteria such as *Escherichia coli* and Klebsiella spp, as well as Gram-positive bacteria such as *Staphylcoccus aureus* and *Streptococcus agalactiae*. The primary treatment for bovine mastitis so far has been the administration of antibiotics such as penicillin. However, the antibiotic therapies currently available for bovine mastitis do not always work, partly because these antibiotics are effective only against Gram-positive pathogens but have poor or strain-dependent activity against Gram-negative pathogens. Thus, there is clearly a need for more effective treatment for mastitis.

The oxazolidinones in the present invention are disclosed in, e.g., U.S. Pat. Nos. 5,688,792 and 6,040,306 and International Publication WO 98/54161, none of which discloses the use of oxazolidinones for treating or preventing mastitis.

Lactoferrin, a glycoprotein present in mammary gland secretions and many other exocrine secretions of mammals, is well known to those skilled in the art. The increased concentrations of endogenous lactoferrin in milk during dry period and the bacteriostatic or bactericidal effects of exogenous lactoferrins are disclosed. See, for example, Smith K L and Oliver S P, Exp. Med. Biol. 137:535–554 (1981); Lohuis, J. A. C. M., Hesen, S M, and Beers H, pages 110–111 in Proc. 3$^{rd}$. Int. IDF Mastitis Sem., Tel Aviv, Israel, A. Saran and S. Soback, ed. M. Lachmann Printers LTD., Haifa, Israel (1995). None of these documents disclose the use of lactoferrin for treating or preventing mastitis.

Under in vitro conditions lactoferrin may enhance the antimicrobial effect of antibiotics against strains of Salmonellae and *Escherichia coli*. See, for example, A. S. Naidu and R. R. Arnold, Diagn. Microbiol. Infect. Dis 20:69–75 (1994); M. S. Sanchez and J. L. Watts, J Dairy Sci. 82: 494–499 (1999). Such enhancing effect of lactoferrins is, however, antibiotic specific. For example, lactoferrins can enhance the antimicrobial effect of erythromycin, ampicillin, ciprofloxacin, chloramphenicol, and rifampicin, but not cefalexin, gentamycin, or polymycin B, against Salmonellae. (A. S. Naidu and R. R. Arnold, Diagn. Microbiol. Infect. Dis 20:69–75 (1994). Thus, none of the prior art teaches or even suggests that lactoferrins may enhance the anti-mastitis effect of the oxazolidinones as disclosed in the present invention.

SUMMARY OF INVENTION

It has been surprisingly found that oxazolidinone is effective in treating and preventing mastitis caused by Gram-negative, as well as by Gram-positive, pathogens in mammals. It has also been surprisingly found that the anti-mastitis effect of oxazolidinone is enhanced by lactoferrins. The oxazolidinones in the present invention are disclosed in, e.g., U.S. Pat. Nos. 5,688,792 and 6,040,306 and International Publication WO 98/54161, none of which discloses the use of oxazolidinones for treating or preventing mastitis. The disclosure of each of U.S. Pat. Nos. 5,688,792 and 6,040,306 and International Publication WO 98/54161 is incorporated here by reference.

Disclosed is a method of treating or preventing mastitis in a mammal, comprising administration to said mammal during dry period of an therapeutically effective amount of an oxazolidinone selected from the group consisting of (S)-N-[[3-[3-fluoro-4-(4-morpholinyl)phenyl]-2-oxo-5-oxazolidinyl]methyl]acetamide and N[[(5S)-3-[3-fluoro-4-(4-thiomorpholinyl)phenyl]-2-oxo-1,3-oxazolidin-5-yl]methyl]acetamide and pharmaceutically acceptable salts thereof.

Also disclosed is a method of treating or preventing mastitis in a mammal, comprising administration to said mammal of an therapeutically effective amount of an oxazolidinone selected from the group consisting of (S)-N-[[3-[3-fluoro-4-(4-morpholinyl)phenyl]-2-oxo-5-oxazolidinyl]methyl]acetamide and N-[[(5S)-3-[3-fluoro-4-(4-thiomorpholinyl)phenyl]-2-oxo-1,3-oxazolidin-5-yl]methyl]acetamide and pharmaceutically acceptable salts thereof, in combination with intramammary administration of a lactoferrin in an amount effective to enhance the therapeutic effect of the oxazolidinone.

Further disclosed is a composition for use in the treatment or prevention of mastitis in a mammal, comprising
  (a) an oxazolidinone selected from (S)-N-[[3-[3-fluoro-4-(4-morpholinyl)phenyl]-2-oxo-5-oxazolidinyl]methyl]acetamide and N-[[(5S)-3-[3-fluoro-4-(4-thiomorpholinyl)phenyl]-2-oxo-1,3-oxazolidin-5-yl]methyl]acetamide or pharmaceutically acceptable salts thereof, and
  (b) a lactoferrin at an amount effective to enhance the therapeutic effect of said oxazolidinone.

DETAILED DESCRIPTION OF THE INVENTION

In one embodiment the invention is directed to a method of treating or preventing mastitis in a mammal comprising administering to said mammal a therapeutically effective amount of an oxazolidinone. In another embodiment the invention is directed to a method of treating or preventing mastitis in a mammal comprising administering to said mammal a therapeutically effective amount of an oxazolidinone in combination with administration of an exogenous lactoferrin at amount effective to enhance the therapeutic effect of the oxazolidinone. In a preferred embodiment the present invention is directed to a method of treating or preventing coliform mastitis in a cow by intramammary infusion of an oxazolidinone during the dry period. These and other embodiments of the present invention will readily occur to those of ordinary skill in the art in view of the disclosure therein.

The following description of the invention concerns mainly with dairy cows; however, it is to be understood that the invention is contemplated with the treatment and prevention of mastitis in all types of mammals.

The oxazolidinones in the present invention are disclosed in, e.g., U.S. Pat. Nos. 5,688,792 and 6,040,306 and International Publication WO 98/54161. Examples of suitable oxazolidinones include (S)-N-[[3-[3-fluoro-4-(4-morpholinyl)phenyl]-2-oxo-5-oxazolidinyl]methyl]acetamide and N-[[(5S)-3-[3-fluoro-4-(4-thiomorpholinyl)phenyl]-2-oxo-1,3-oxazolidin-5-yl]methyl]acetamide, and pharmaceutically acceptable salts thereof.

The active agents of the subject invention can be given to a mammal either after the onset of mastitis, thus serving as a treatment, or prior to the onset of mastitis, thus serving as a preventive measure. The preventive use of the subject invention is particularly important, for instance, in case mastitis has been detected in some animals in the same herd. It is often desirable to treat all animals in same herd affected in order to eliminate the infection from the whole herd.

Regardless of whether the oxazolidinones are used to treat or prevent mastitis, the oxazolidinones can either be used individually, in combination with each other, or in combination with exogenous lactoferrins. When used during the dry period, the oxazolidinones are preferred to be administered without exogenous lactoferrins. When used during lactation period, the oxazolidinones are preferred to be administered in combination with the administration of exogenous lactoferrins.

Regardless of whether or not lactoferrins are administered, the oxazolidinones are administered either intramammarily or systemically. Intramammary administration, however, is the preferred route when the oxazolidinones are administered in combination with lactoferrins.

When administered intramammarily, the oxazolidinones are administered by injection into the mammary gland, typically by infusion into the teat through the milk canal. The dosage of the oxazolidinones by intramammary injection is from about 25 mg to about 1000 mg, and preferably from about 125 mg to about 500 mg. The oxazolidinones are typically given once.

When administered systemically, the oxazolidinones are administered parenterally or orally, and typically once per day for three or more consecutive days.

When administered orally, the oxazolidinones can be administered in tablet, capsule or liquid (suspension or solution) dosage form in a pharmaceutically acceptable vehicle. The oxazolidinones can also be administered in feed or drinking water. Oral administration in any of these dosage forms is well known in the art and may be carried out in ways common in the animal veterinary medical art. Regardless of the dosage form, the anti-mastitis effective amount of the oxazolidinones is from about 1 mg/kg/day to about 10 mg/kg/day, and preferably from about 2.5 mg/kg/day to about 5 mg/kg/day.

When administered parenterally, the oxazolidinones are administered by subcutaneous, intradermal, intramuscular, or intravenous injection. Parenteral administration is well known in the art and may be carried out in ways common in the animal veterinary or human medical art. When prepared as injectables, the oxazolidinones are usually prepared as liquid formulations in a pharmaceutically acceptable vehicle as is known to those skilled in the art. Regardless of the route, the daily dosage of the oxazolidinones by patrenteral administration is from about 1 mg/kg/day to about 10 mg/kg/day, and preferably from about 2.5 mg/kg/day to about 5 mg/kg/day.

The exact dosage and frequency duration of administration of the oxazolidinones may be changed in response to numerous variables such as the particular oxazolidinone used, the severity of the condition being treated, the general physical condition of the animal, the response of the animal to the treatment, the size of the animal, and whether lactoferrin is used and the dosage thereof.

When lactoferrin is used in combination with the oxazolidinones, the lactoferrin should be administered via intramammary injection, typically by infusion into the teat through the milk canal, and in the same frequency and duration as the oxazolidinones.

Lactoferrin is formulated as a liquid dosage form (solution or suspension) in a pharmaceutically acceptable vehicle as is known to those skilled in the art, and is preferably formulated together with the oxazolidinone as a liquid dosage form (solution or suspension) in a composite formulation.

In another embodiment, the invention is directed to a composition for use in the treatment or prevention of mastitis in a mammal, comprising (a) an oxazolidinone and (b) a lactoferrin at an amount effective to enhance the therapeutic effect of said oxazolidinone. The composition should be prepared in liquid dosage forms in any pharmaceutically acceptable carriers as are known in the art. The composition is preferably administered by intramammary injection.

When formulated together with the oxazolidinone in a composite formulation, the lactoferrin is administered simultaneously with the oxazolidinones. When formulated separately from the oxazolidinones, the lactoferrin is typically administered within 1 hour of the oxazolidinone administration. The amount of lactoferrin effective to enhance the anti-mastitis effect of the oxazolidinones is from about 0.5 g to about 5 gram, and preferably from about 2 g to about 3 g, regardless of the size and species of the animal being treated. The exact dosage and frequency and duration of administration of the lactoferrin may be changed in response to numerous variables, such as the particular oxazolidinone used and the dosage thereof, the severity of the condition being treated, the general physical condition of the animal, the response of the animal to the treatment, and levels of endogenous lactoferrins.

Definitions and Conventions

The definitions and explanations below are for the terms as used throughout this entire document including both the specification and the claims.

Definitions

A "therapeutically effective amount" of oxazolidinones refers to any amount of the oxazolidinones, administered either individually, in combination with each other or with lactoferrin, that is sufficient to either treat or prevent mastitis in a mammal to which the oxazolidinones are administered.

"Pharmaceutically acceptable" refers to those properties and/or substances which are acceptable to the animal from a pharmacological/toxicological point of view and to the manufacturing pharmaceutical chemist from a physical/chemical point of view regarding composition, formulation, stability, animal tolerance and bioavailability.

"Oxazolidinones" refer to the compounds of EXAMPLES 1 and 2.

"Treating mastitis" refers to ameliorating an animal that has contacted mastitis.

"Preventing mastitis" refers to suppressing the occurrence, severity, and duration of mastitis if it is later contacted.

"Dry period" refers to the time period during which the mammal is non-lactating.

EXAMPLES

Without further elaboration, it is believed that one skilled in the art can, using the preceding description, practice the present invention to its fullest extent. The following detailed examples describe how to practice the invention and are to be construed as merely illustrative, and not limitations of the preceding disclosure in any way whatsoever.

Example 1

(S)-N-[[3-[3-fluoro-4-(4-morpholinyl)phenyl]-2-oxo-5-oxazolidinyl]methyl]acetamide Example 2

(2)N-[[(5S)-3-[3-fluoro-4-(4-thiomorpholinyl)phenyl]-2-oxo-1,3-oxazolidin-5-yl]methyl]acetamide.

Example 3

A 3-lactation cow in dry period with moderate mastitis is administered 300 mg of the oxazolidinone in EXAMPLE 1, once per day for 5 days. The oxazolidinone is formulated as a solution and administered by intramammary infusion. At the end of the treatment the cow is examined and the mastitis is gone.

Example 4

A 2-lactation cow without mastitis is administered a single dose of 250 mg of the oxazolidinone in EXAMPLE 2 at the start of dry off period. The oxazolidinone is formulated as a solution and administered by intramammary infusion. Although mastitis occurs in other dry cows that are in the same herd but are not treated with the oxazolidinones, the cow treated is not infected.

Example 5

A 3-lactation cow in lactation with moderate mastitis is administered 300 mg of the oxazolidinone in EXAMPLE 2 in combination with administration of 3 g of bovine lactoferrin, once per day for 5 consecutive days. The oxazolidinone and the lactoferrin are prepared in a composite suspension formulation and administered by intramammary infusion. At the end of the treatment the cow is examined and the mastitis is gone.

What is claimed is:

1. A method of treating or preventing mastitis caused by *Escherichia coli* in a mammal, comprising administration to said mammal during dry period of an therapeutically effective amount of an oxazolidinone selected from the group consisting of (S)-N-[[3-[3-fluoro-4-(4-morpholinyl)phenyl]-2-oxo-5-oxazolidinyl]methyl]acetamide and N-[[(5S)-3-[3-fluoro-4-(4-thiomorpholinyl)phenyl]-2oxo-1,3-oxazolidin-5-yl]methyl]acetamide and pharmaceutically acceptable salts thereof.

2. The method of claim 1 wherein said administration is done prior to the onset of the infection.

3. The method of claim 1 wherein said administration is done after the onset of the infection.

4. The method of claim 1 wherein the mammal is a cow, goat, or ewe.

5. The method of claim 4 wherein the mammal is a cow.

6. The method of claim 1 wherein the administration of the oxazolidinone is via intramammary injection.

7. The method of claim 6 wherein the oxazolidinone is administered at an amount from about 25 mg to about 1000 mg.

8. The method of claim 7 wherein the oxazolidinone is administered at an amount from about 125 mg to about 500 mg.

9. The method of claim 1 wherein the administration of the oxazolidinone is done systemically.

10. The method of claim 10 wherein the daily dose of the oxazolidinone is from about 1 mg/kg to about 10 mg/kg.

11. The method of claim 10 wherein the daily dose of the oxazolidinone is from about 2.5 mg/kg to about 5 mg/kg.

12. The method of claim 1 wherein the administration of the oxazolidinone is during dry period.

13. A method of treating or preventing mastitis in a mammal, comprising administration to said mammal of an therapeutically effective amount of an oxazolidinone selected from the group consisting of (S)-N-[[3-[3-fluoro-4-(4-morpholinyl)phenyl]-2-oxo-5-oxazolidinyl]methyl]acetamide and N-[[(5S)-3-[3-fluoro-4-(4-thiomorpholinyl)phenyl]-2-oxo-1,3-oxazolidin-5-yl]methyl]acetamide and pharmaceutically acceptable salts thereof, in combination with intramammary administration of a lactoferrin in an amount effective to enhance the therapeutic effect of the oxazolidinone.

14. The method of claim 13 wherein the lactoferrin is a bovine lactoferrin.

15. The method of claim 13 wherein the administration of both the oxazolidinone and lactoferrin is done prior to the onset of the infection.

16. The method of claim 13 wherein the administration of both the oxazolidinone and lactoferrin is done after the onset of the infection.

17. The method of claim 13 wherein the mastitis is caused by *Escherichia coli*.

18. The method of claim 13 wherein the mammal is a cow, goat, or ewe.

19. The method of claim 13 wherein the mammal is a cow.

20. The method of claim 13 wherein the administration of the oxazolidinone is via intramammary injection.

21. The method of claim 20 wherein the amount of oxazolidinone to be administered is from about 25 mg to about 1000 mg.

22. The method of claim 20 wherein the amount of the oxazolidinone to be administered is from about 125 mg to about 500 mg.

23. The method of claim 13 wherein the administration of the oxazolidinone is done systemically.

24. The method of claim 23 wherein the daily dose of the oxazolidinone to be administered is from about 1 mg/kg/day to about 10 mg/kg/day.

25. The method of claim 23 wherein the daily dose of the oxazolidinone to be administered is from about 2.5 mg/kg/day to about 5 mg/kg/day.

26. The method of claim 13 wherein the amount of lactoferrin to be administered is from about 0.5 g to about 5 g.

27. The method of claim 13 wherein the amount of lactoferrin to be administered is from about 2 g to about 3 g.

28. The method of claim 13 wherein the administration of both the oxazolidinone and the lactoferrin is done during dry period.

29. The method of claim 13 wherein the administration of both the oxazolidinone and the lactoferrin is done during lactation period.

30. A composition for use in the treatment or prevention of mastitis in a mammal, comprising
    (a) an oxazolidinone selected from (S)-N-[[3-[3-fluoro-4-(4-morpholinyl)phenyl]-2-oxo-5-oxazolidinyl]methyl]acetamide and N-[[(5S)-3-[3-fluoro-4-(4-thiomorpholinyl)phenyl]-2-oxo-1,3-oxazolidin-5-yl]methyl]acetamide or pharmaceutically acceptable salts thereof, and
    (b) a lactoferrin at an amount effective to enhance the therapeutic effect of said oxazolidinone.

31. The composition of claim 30 wherein said lactoferrin is a bovine lactoferrin.

* * * * *